United States Patent [19]
Bieniarz et al.

[11] Patent Number: 6,100,434
[45] Date of Patent: Aug. 8, 2000

[54] METHOD FOR SYNTHESIZING SEVOFLURANE AND AN INTERMEDIATE THEREOF

[75] Inventors: Christopher Bieniarz, Highland Park; Kornepati V. Ramakrishna, Libertyville; Christopher Behme, Lake Villa, all of Ill.

[73] Assignee: Abbott Laboratories, Abbott Park, Ill.

[21] Appl. No.: 09/280,794

[22] Filed: Mar. 26, 1999

[51] Int. Cl.$^7$ .............................. C07C 41/09; C07C 41/22
[52] U.S. Cl. .................... 568/683; 568/681; 568/682; 568/684
[58] Field of Search ..................... 568/683, 681, 568/684, 682

[56] References Cited

U.S. PATENT DOCUMENTS

| | | | |
|---|---|---|---|
| 2,992,276 | 7/1961 | Weinmayr | 568/683 |
| 3,476,860 | 11/1969 | Croix et al. | 514/722 |
| 3,683,092 | 8/1972 | Regan et al. | 514/723 |
| 3,689,571 | 9/1972 | Regan et al. | 260/614 F |
| 4,250,334 | 2/1981 | Coon et al. | 568/683 |
| 4,469,898 | 9/1984 | Coon et al. | 568/683 |
| 4,874,901 | 10/1989 | Halpern et al. | 568/683 |
| 5,811,596 | 9/1998 | Kawai et al. | 568/683 |
| 5,886,239 | 3/1999 | Kudzma et al. | 568/684 |

*Primary Examiner*—Deborah D. Carr
*Assistant Examiner*—Rosalynd Keys
*Attorney, Agent, or Firm*—Brian R. Woodworth

[57] ABSTRACT

A method for synthesizing fluoromethyl-1,1,1,3,3,3-hexafluoroisopropyl ether. The method includes the step of combining in the presence of aluminum trichloride a quantity of hexafluoroisopropanol and a quantity of either 1,3,5-trioxane or paraformaldehyde to produce sevochlorane. The resulting sevochlorane is then combined with an alkali metal fluoride to produce fluoromethyl-1,1,1,3,3,3-hexafluoroisopropyl ether.

32 Claims, 3 Drawing Sheets

METHOD FOR SYNTHESIZING SEVOFLURANE AND AN INTERMEDIATE THEREOF

TECHNICAL FIELD OF THE INVENTION

The present invention relates generally to a method for producing the inhalation anesthetic sevoflurane and an intermediate useful in producing sevoflurane.

BACKGROUND OF THE INVENTION

Sevoflurane (fluoromethyl-1,1,1,3,3,3-hexafluoroisopropyl ether) is an inhalation anesthetic and is described in U.S. Pat. No. 3,689,571 which is incorporated herein by reference. U.S. Pat. Nos. 4,250,334 and 4,469,898 describe techniques for producing sevoflurane. The '334 and '898 patents also are incorporated herein by reference. The techniques described in these patents utilize hexafluoroisopropyl alcohol (HFIP) as a starting material. The '898 patent describes a technique in which HFIP is combined with formaldehyde, hydrogen fluoride, and a protonating, dehydrating and fluoride ion-generating agent. The '334 patent describes a technique in which HFIP is added to a mixture of a stoichiometric excess of paraformaldehyde and hydrogen fluoride, plus sufficient sulfuric acid to sequester most of the water produced by the reaction.

Sevoflurane produced in accordance with the techniques described in the '334 and '898 patents must undergo additional purification steps due to the fact that the polyacetal formed in the first step of the described techniques is cleaved into numerous by-products, primarily fluorinated bis-ethers. Such by-products can be difficult to remove from the reaction solution. Further, the use of corrosive materials such as hydrogen fluoride and sulfuric acid requires that specialized equipment and special handling precautions be employed during the described processes, thereby increasing the cost of sevoflurane production.

It is desirable to provide a process that produces sevoflurane in relatively high yields, i.e., at least about 80% yields. It also is desirable to provide a process that is relatively simple, i.e., a process that requires a minimum number of steps and a minimum number of reaction vessels. Finally, it is desirable to provide a process for producing sevoflurane that utilizes commercially available, non-corrosive, and relatively inexpensive materials.

SUMMARY OF THE INVENTION

The present invention is directed to a method for synthesizing fluoromethyl-1,1,1,3,3,3-hexafluoroisopropyl ether (sevoflurane). In a first embodiment of the process of the present invention, hexafluoroisopropanol (HFIP) is reacted with a first compound selected from a group consisting of 1,3,5-trioxane and paraformaldehyde in the presence of aluminum trichloride in order to produce an intermediate, chloromethyl-1,1,1,3,3,3-hexafluoroisopropyl ether (sevochlorane). The sevochlorane intermediate is then reacted with a second compound selected from a group consisting of KF, NaF, $KF_2H$, and $NaF_2H$ in order to produce sevoflurane.

The present invention is further directed to chloromethyl-1,1,1,3,3,3-hexafluoroisopropyl ether and a method for producing it. In a first embodiment of this process, hexafluoroisopropanol (HFIP) is reacted with a first compound selected from a group consisting of 1,3,5-trioxane and paraformaldehyde in the presence of aluminum trichloride in order to produce chloromethyl-1,1,1,3,3,3-hexafluoroisopropyl ether.

The present invention is still further directed to a method for synthesizing fluoromethyl-1,1,1,3,3,3-hexafluoroisopropyl ether (sevoflurane) from chloromethyl-1,1,1,3,3,3-hexafluoroisopropyl ether. In a first embodiment of this process, chloromethyl-1,1,1,3,3,3-hexafluoroisopropyl ether is reacted with a compound selected from a group consisting of KF, NaF, $KF_2H$, and $NaF_2H$ in order to produce sevoflurane.

Other aspects of the present invention will be apparent from reading the following detailed description of the invention and the appended claims.

DETAILED DESCRIPTION OF THE INVENTION

Although the present invention is disclosed herein in connection with certain examples and preferred embodiments, it will be appreciated that various modifications of the invention can be made without departing from the spirit and scope of the present invention.

Figure 1:
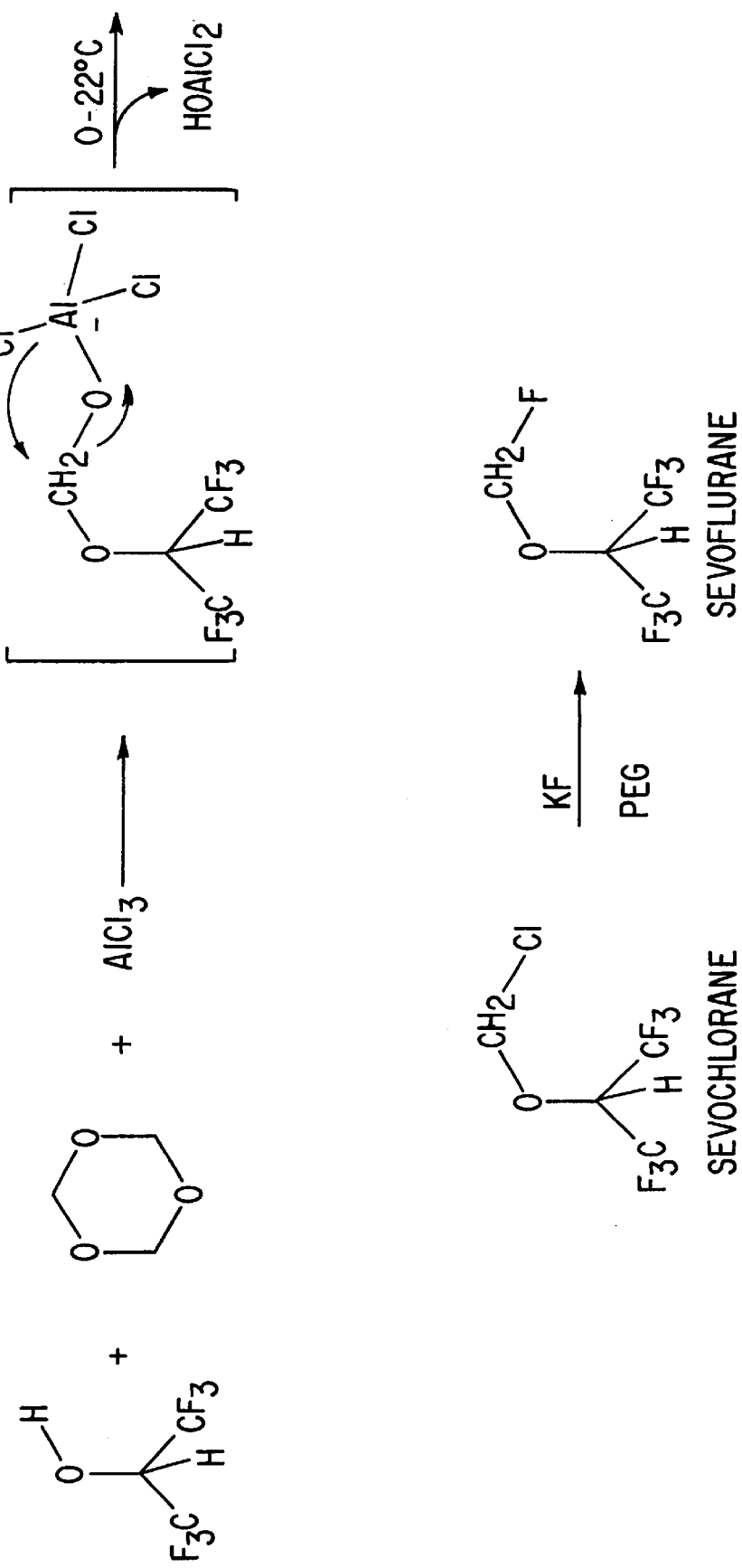
FIG. 1 depicts a reaction schematic of a first embodiment of the method of the present invention.

A representative reaction scheme for the method of the present invention is set forth in FIG. 1. The examples set forth herein are provided for the purpose of giving greater insight into the processes of the present invention. It is to be appreciated that the reaction scheme set forth in FIG. 1 and the examples set forth herein are provided for the purpose of providing a clearer understanding of the present invention, and that they are not intended to be limiting. The scope of the present invention is defined by the appended claims.

As set forth in detail herein, it is possible to perform the method of the present invention in a single pot, although it will be appreciated that the described method can be practiced in multiple pots. A "single pot" process is a process that can be performed in a single reaction vessel. It will be appreciated by those of ordinary skill that single pot processes provide certain advantages over multiple pot processes. For example, single pot processes require less handling and/or transfer of components, thereby reducing the risk of accident or mistake. Single pot processes also tend to be less expensive than multiple pot processes as a result of the reduction in handling and transfer of reaction ingredients.

In accordance with the embodiment of the method of the present invention depicted in FIG. 1, fluoromethyl-1,1,1,3,3-hexafluoroisopropyl ether (sevoflurane) is prepared by reacting 1,1,1,3,3,3-hexafluoroisopropanol (HFIP) with 1,3,5-trioxane (trioxane) in the presence of aluminum trichloride. In an alternate embodiment, paraformaldehyde is used in lieu of 1,3,5-trioxane. It will be appreciated by those of ordinary skill in the art that HFIP, 1,3,5-trioxane, paraformaldehyde, and aluminum trichloride are commercially available materials and that their use does not present significant safety concerns.

The first step of the reaction of the present invention is exothermic. When paraformaldehyde is used in place of trioxane, the exotherm is rapid and relatively violent. The first step of the method of the present invention is slower and more readily controlled when trioxane is used, although both trioxane and paraformaldehyde are efficacious when used in connection with the method of the present invention.

Aluminum trichloride serves to activate the 1,3,5-trioxane or paraformaldehyde used in the first step of the method of the present invention. Aluminum trichloride further acts as a chlorinating agent, i.e., a source of chlorine, and as a dehydrating agent in the first step of the reaction of the present invention.

It will be appreciated that other chlorinating agents can be used in connection with the method of the present invention. For example, $PCl_3$ can be used in lieu of aluminum trichloride. However, Applicants have discovered that aluminum trichloride is preferable when used in connection with the method of the present invention.

In the first step of the reaction scheme depicted in FIG. 1, one molar equivalent of HFIP, 0.33 molar equivalent of 1,3,5-trioxane, and 1 molar equivalent of aluminum trichloride are combined to produce an aluminum hydroxydichloride ($HOAlCl_2$) polymer and chloromethyl-1,1,1,3,3,3-hexafluoroisopropyl ether (sevochlorane). This first reaction step can be conducted at room temperature, i.e., approximately 25° C. In a preferred embodiment, the first reaction step is completed at a temperature of 0°–22° C.

Figure 2:
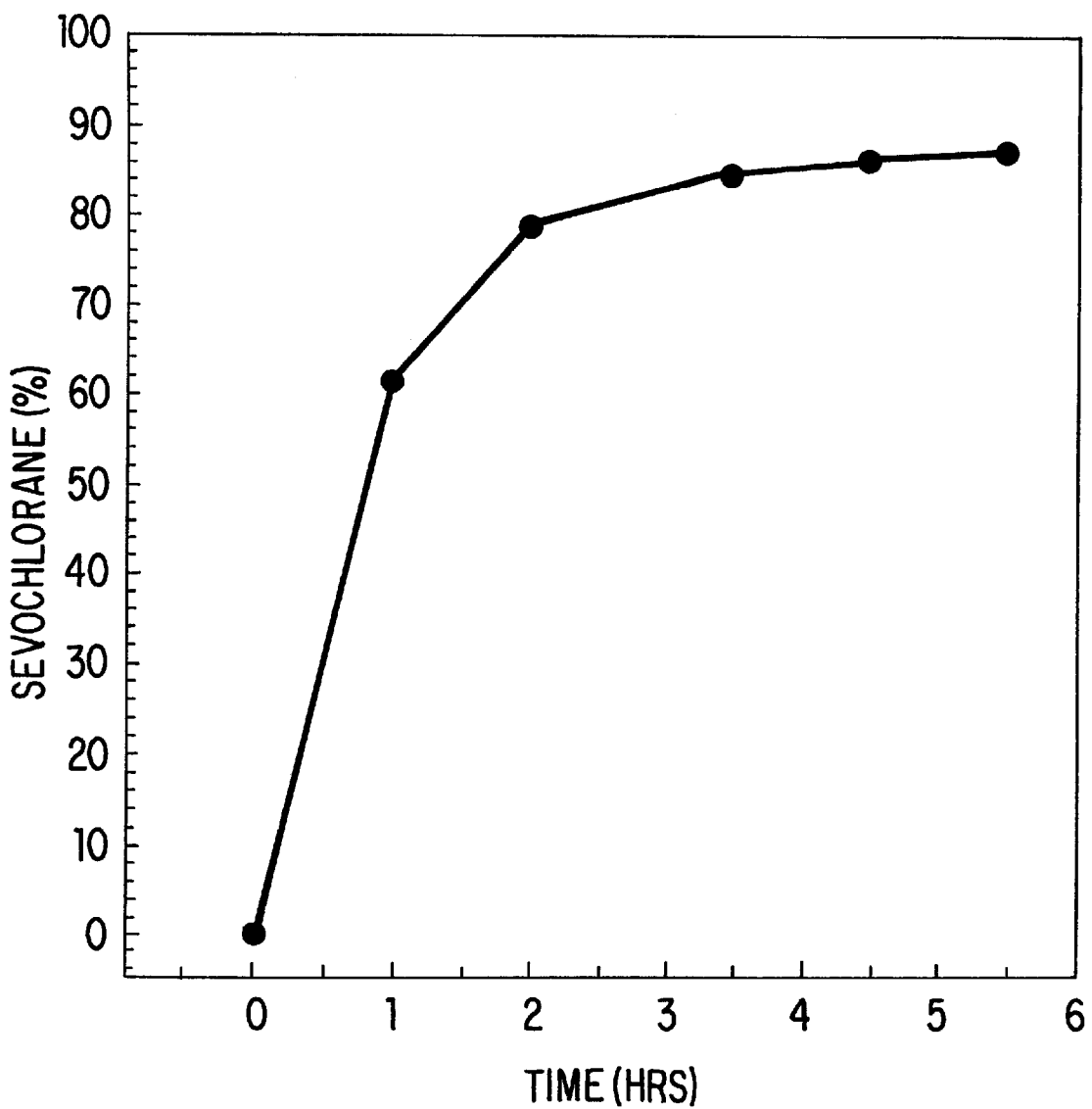
FIG. 2 depicts the rate of conversion of HFIP to sevochlorane at 5° C. in accordance with the first embodiment of the method of the present invention.

It will be appreciated that the time required to complete the first reaction step will vary depending upon the temperature at which the reaction occurs, i.e., the higher the temperature, the faster the reaction. FIG. 2 depicts the production of sevochlorane from HFIP when the first reaction step is performed at approximately 5° C.

It has been discovered that the aluminum hydroxydichloride polymer produced in the first step of the reaction of the present invention can have deleterious effects upon sevochlorane, and upon sevoflurane, due to its degradative effects thereon. In particular, the aluminum in the resulting polymer can act as a Lewis acid to cause degradation of sevochlorane and sevoflurane. Accordingly, the aluminum hydroxydichloride polymer produced by the first reaction step preferably is removed or otherwise neutralized, thereby preventing degradation of the sevochlorane and/or sevoflurane produced in accordance with the method of the present invention.

Removal of the aluminum hydroxydichloride can be effected by precipitating the aluminum hydroxydichloride polymer and separating the precipitate from the remaining products of the first reaction step. The separated aluminum hydroxydichloride can then be recycled and further processed to provide additional aluminum trichloride for use in connection with the method of the present invention. Appropriate methods for the recycling of aluminum hydroxydichloride will be apparent to those of ordinary skill in the pertinent art.

In a preferred embodiment of the method of the present invention, the $HOAlCl_2$ polymer produced by the first reaction step is decomposed using an aqueous acid. For example, aqueous hydrochloric acid (HCl) can be added to the products of the first reaction step in order to decompose the $HOAlCl_2$ polymer. For example, 1 N–12 N HCl, and more preferably 4 N–6 N HCl, can be used in order to decompose the $HOAlCl_2$ polymer. It will be appreciated that other known aqueous acids can be used in lieu of hydrochloric acid.

The water in the aqueous acid used to decompose the $HOAlCl_2$ polymer acts as a Lewis base or a Lewis acid inhibitor in order to neutralize the aluminum in the polymer, thereby preventing the aluminum in the polymer from causing the degradation of sevochlorane produced in accordance with the first step of the method of the present invention.

The decomposed $HOAlCl_2$ polymer can be removed from the reaction vessel using a variety of known techniques.

In an alternative embodiment, a molar excess of KF, or a molar excess of another alkali metal fluoride, is used in lieu of an aqueous acid in order to neutralize the $HOAlCl_2$.

The intermediate produced as a result of the first reaction step, i.e., sevochlorane, is then preferably reacted in a second reaction step with 1–5 molar equivalents, e.g., 5 molar equivalents, of an alkali metal fluoride selected from the first column of the periodic table. The alkali metal fluoride acts as a fluorinating agent in the production of sevoflurane from sevochlorane. In the embodiment of the present invention depicted in FIG. 1, potassium fluoride (KF) is used to fluorinate sevochlorane and thereby produce sevoflurane. Other alkali metal fluorides selected from the first column of the periodic table that are useful in the second reaction step of the present invention include, but are not necessarily limited to, NaF; $KF_2H$; and $NaF_2H$. However, due to the acidic nature of $KF_2H$ and $NaF_2H$, it advantageous to add 1–3 molar equivalent, e.g., 2 molar equivalent, of either sodium carbonate ($Na_2CO_3$) or potassium carbonate ($K_2CO_2$) in order to neutralize the acidity of these alkali metal fluorides when either is used in the second step of the reaction of the present invention. Applicants believe that KF is the preferred salt due to the high yields of sevoflurane resulting from its use in accordance with the reaction of the present invention.

The second reaction step preferably is conducted in the presence of a solvent. For example, N-methyl pyrrolidone, ethylene glycol, water, t-butanol, higher (i.e., $C \geq 5$) alkyl non-nucleophilic alcohols, and phenols can be used as solvents in the second reaction step. In a preferred embodiment, a solvent having the formula $HO-(CH_2-CH_2-O)_nH$, where n=1–20, and preferably where n=2–15, is used as a solvent in connection with the second reaction step of the method of the present invention. For example, polyethylene glycol (PEG) 400 has been found to provide optimal results when used as a solvent in the second reaction step of the present invention. PEG 400 is a well-known polyethylene glycol having an average molecular weight of 400 and an n value of 8–10.

Other solvents useful in connection with the second reaction step of the present invention include, but are not necessarily limited to, dimethyl sulfoxide (DMSO), dimethyl formamide (DMF), hexamethyl phosphoramide (HMPA) and ethers of polyethylene glycols, i.e., glymes. In addition, a non-polar solvent can be used in combination with a phase transfer catalyst in connection with the second reaction step of the present invention. For example, methyl trialkyl ($C_8$–$C_{10}$) ammonium chloride can be used as a phase transfer catalyst in combination with a non-polar solvent in connection with the process of the present invention. Water and polar solvents also can be used in connection with the second reaction step.

Unlike previous methods for producing sevoflurane, such as the method disclosed in U.S. Pat. No. 4,874,901, the second reaction step preferably is conducted in the presence of water. For example, water can be present in an amount from 0.1%–99.9%, weight-for-weight relative to the above-discussed solvent. In a preferred embodiment, water is present in an amount of 0.1%–5%, weight-for-weight, relative to the above-discussed solvent. It has been discovered that higher levels of water may tend to cause hydrolysis of sevochlorane, thereby producing HFIP. Further, it has been discovered that higher levels of water may tend to impede the second reaction step due to the relative immiscibility of sevochlorane in water. It will be appreciated that water will act as a co-solvent when used in connection with the second reaction step of the method of the present invention.

Although the second step of the reaction of the present invention is preferably conducted in the presence of water, it will be appreciated that the production of sevoflurane from sevochlorane in accordance with the method of the present invention can be performed under anhydrous conditions.

The water used in the second step of the reaction also acts as a Lewis base (Lewis acid inhibitor) in order to preclude the degradation of the sevoflurane produced in the second reaction step by aluminum impurities that may be present in the reaction vessel as a result of the first reaction step. It will be appreciated that the presence of water, and its Lewis base function, will be particularly important in those situations in which the method of the present invention is practiced in a single pot process, i.e., wherein the first and second reaction steps are practiced in a single reaction vessel.

The second step of the reaction of the present invention can be conducted at a variety of temperatures. For example, if a polyethylene glycol solvent is used in the second reaction step, a temperature of 85°–95° can be used. It is believed that higher temperatures will be required if a solvent other than polyethylene glycol is used. The reaction step preferably is allowed to progress to completion, with the completion time being contingent upon the temperature at which the second step of the reaction occurs.

Sevoflurane produced in accordance with the method of the present invention can be isolated from the resulting reaction mixture using known distillation techniques, e.g., flash distillation. In one embodiment of the present invention, sevoflurane is isolated from the products of the second reaction step by the addition of water into the resulting products. Sevoflurane is not soluble in water and therefore separates as a lower layer in the reaction vessel. In contrast, any impurities and solvents present in the products of the second reaction step are soluble in water and will therefore be present in the water in the reaction vessel. The sevoflurane can be separated from the water containing the dissolved impurities and solvents using known techniques.

Figure 3:
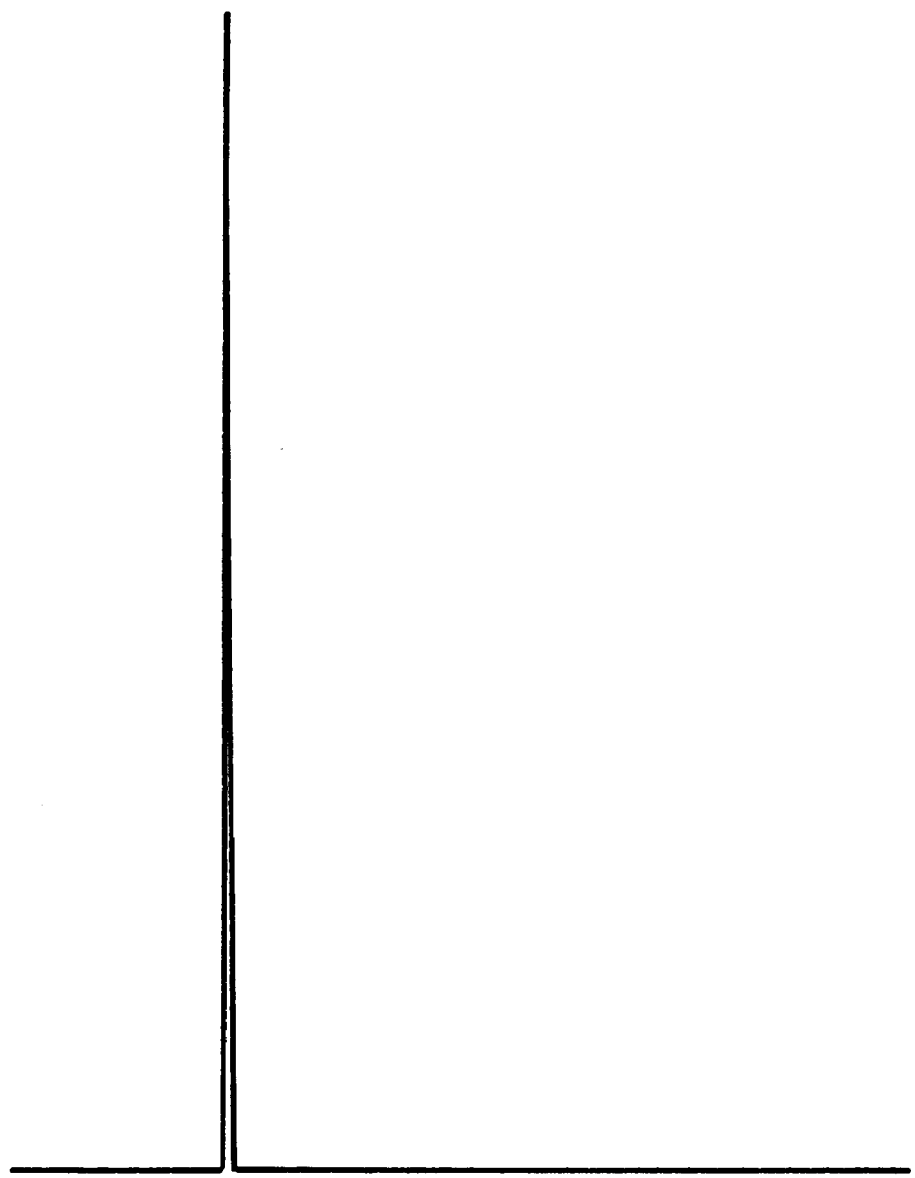
FIG. 3 depicts a gas chromatographic analysis of sevoflurane produced in accordance with the first embodiment of the method of the present invention after a single flash distillation of the product of the reaction.

It has been found that the method of the present invention produces a substantially 100% conversion of sevochlorane into sevoflurane, as measured by gas chromatography and other analytical methodologies. FIG. 3 shows that the purity of sevoflurane produced in accordance with the method of the preset invention approaches 100%.

The method of the present invention will be further understood in view of the following examples. However, the following examples are not intended to limit the scope of the invention in any way, the scope of the invention being defined by the appended claims.

EXAMPLE 1
Synthesis of Sevochlorane

Into a dry 100 ml round-bottomed flask equipped with a magnetic stir bar was placed anhydrous aluminum chloride (18.56 g, 139.2 mmol), and the flask was stoppered to prevent hydrolysis by adventitious moisture. The flask containing the dry reagent was placed in an ice water bath and HFIP (14.66 ml, 139.2 mmol) was added in a single portion. The reaction flask was loosely stoppered such that any HCl gas evolved could vent from the flask. The mixture was stirred at 0° C. for 10 minutes, at which time gas evolution had ceased. To the reaction mixture was added 1,3,5-trioxane (4.179 g, 46.4 mmol) in a single portion, and the reaction flask was capped with a rubber septum which was vented via a manifold to an oil bubbler. The ice water bath was removed and the reaction mixture was allowed to warm to ambient temperature and stirred overnight (approximately 20 hours). The reaction mixture was then cooled to 0° C. in an ice water bath and the rubber septum was replaced with a dry ice/acetone cooled condenser. To the cooled reaction mixture was added 50 ml of cold (−20° C.) 6 N aqueous HCl, in small portions over the course of 5–10 minutes. After the addition was complete, the evolution of HCl gas subsided and the reaction flask/condenser assembly was agitated manually to complete the hydrolysis of the polymeric aluminum salts. Water was added (approximately 50 ml) in an amount sufficient to dissolve any solid material until the cloudy solution became clear. The mixture was poured into a separatory funnel and partitioned. The product (bottom layer) was drawn off and placed in a tared flask and capped. The yield of crude product was 27.00 g, 87%. The crude product mix was qualitatively assayed by GC/MS as follows: HFIP chloromethyl ether 74%, bis HFIP acetal 22%, HFIP 2%, and polyketals <2%. Subsequent quantitative analysis by integration of the methylene singlets of the chloromethyl ether and bis acetal in the 300 MHz H NMR spectrum of the crude product mix revealed the composition, reported by mass, as follows:

| | |
|---|---|
| sevochlorane | 95% |
| bis-HFIP-acetal | <5% |
| water | <1% |
| polyketals | <1% |

EXAMPLE 2
Conversion of Sevochlorane to Sevoflurane

To a solution of sevochlorane (2.16 grams, 10 mmol) in diethylene glycol (10 ml), KF (2.32 grams, 40 mmol) was added at room temperature. The reaction flask was fitted with a cold (5° C.) water condenser and the reaction mixture was heated to 95° C. After 1 hour, GC-MS analysis of an ether extract of the reaction mixture indicated the complete consumption of sevochlorane and the formation of sevoflurane. The reaction flask was cooled to room temperature and water (30 ml) was added to the colorless reaction mixture and stirred vigorously resulting in the separation of the product as a bottom layer. The flask was fitted with a distillation head and a receiving flask immersed in an oil bath was heated to 95° C. Sevoflurane (1.42 grams, 71% yield) distilled at 58° C.

In this example, sevoflurane was distilled directly from the reaction mixture after it has been diluted with water. Alternatively, the bottom layer of the reaction mixture can be separated and then distilled. This addition of water is required to decomplex sevoflurane from the solvent, thereby facilitating the distillation.

EXAMPLE 3
Single Pot Preparation of Sevoflurane From HFIP

Into a 50 liter glass reaction vessel fitted with a mechanical stirrer, a temperature sensing device, a condenser (cooled to 0°–10° C.), and cooling coils, were placed anhydrous aluminum trichloride (4316 g, 32.37 moles, 1.00 equivalent). Scrubbers containing water were attached to the reactor to absorb any hydrogen chloride gas evolved in the reaction. The aluminum trichloride was cooled to 0° C. and hexafluoroisopropanol (5540 g, 3360 ml, 32.37 moles, 1.00 equivalent) was added in a single portion while stirring. The reaction was allowed to remain at 0° C. until HCl gas evolution had ceased and a homogeneous slurry was formed. 1,3,5-trioxane (972 g, 10.79 moles, 0.33 equivalent) was then added. The temperature of the reaction increased to 8° C. Next, the reaction mixture was cooled to 0° C. and 13.3 liters of ice cold 6 N HCl was added slowly with vigorous stirring. The quench was exothermic, and therefore the temperature was maintained between 40° and 60° C. When the addition of HCl solution no longer produced an exotherm, the remainder of the HCl solution was added rapidly. Water (5 liters) was then added to dissolve the solids and stirring continued until two clear phases had formed. The water layer was siphoned off and the organic layer was washed twice more with water (5 liters). A distillation receiver was attached to the reaction vessel. Dry ice traps were also added to the system to collect any volatilized sevoflurane. PEG 400 (16 liters, 44.31 moles, 1.37 equivalent) was added to the reaction vessel with stirring. Karl Fisher analysis showed a water content of 3.2%. Spray dried KF (5651 g, 97.26 moles, 3.00 equivalent) was then added in portions. The reaction mixture was heated to an internal temperature of 78° C. for approximately 2.5 hours. A gas chromatographic analysis of the reaction mixture indicated that all of the sevochlorane had been consumed. The crude sevoflurane (4365 g) which distilled out of the reactor was dried over $MgSO_4$. The reaction vessel was cooled to room temperature, diluted with water (15 liters) and heated to afford an additional amount of sevoflurane (427 g) which distilled out between 100° and 110°. This sevoflurane also was dried over $MgSO_4$. Distillation of the crude sevoflurane (4792 g) thus obtained was conducted using a 1 ft. vigreaux distillation column to provide sevoflurane (3997 g) having a purity of approximately 99.4%.

The present invention further is directed to a method for preparing sevochlorane, as described in detail herein in connection with the first step of the method for producing sevoflurane.

The present invention is directed to a method for preparing sevoflurane which employs sevochlorane as a starting material. The details of this method are described in detail herein in connection with the second reaction step of the method for producing sevoflurane from HFIP discussed in detail herein.

Although present invention has been described herein in connection with certain preferred embodiments and certain examples, it will be appreciated by one of ordinary skill in the pertinent art that various modifications are possible without departing from the scope of the appended claims.

What is claimed is:

1. A method for synthesizing fluoromethyl-1,1,1,3,3,3-hexafluoroisopropyl ether, said method comprising:
   combining hexafluoroisopropanol and a first compound in the presence of a chlorinating agent to produce an intermediate, said first compound being selected from a group consisting of 1,3,5-trioxane and paraformaldehyde, said chlorinating agent being selected from a group consisting of aluminum trichloride and phosphorous trichloride;
   combining said intermediate and a second compound selected from a group consisting of KF, NaF, $KF_2H$, and $NaF_2H$ to produce fluoromethyl-1,1,1,3,3,3-hexafluoroisopropyl ether.

2. A method for synthesizing fluoromethyl-1,1,1,3,3,3-hexafluoroisopropyl ether in accordance with claim 1, wherein said first compound is 1,3,5-trioxane.

3. A method for synthesizing fluoromethyl-1,1,1,3,3,3-hexafluoroisopropyl ether in accordance with claim 1, wherein said chlorinating agent is aluminum trichloride.

4. A method for synthesizing fluoromethyl-1,1,1,3,3,3-hexafluoroisopropyl ether in accordance with claim 1, wherein said second compound is KF.

5. A method for synthesizing fluoromethyl-1,1,1,3,3,3-hexafluoroisopropyl ether in accordance with claim 1, wherein combining said intermediate and said second compound is performed in the presence of a solvent.

6. A method for synthesizing fluoromethyl-1,1,1,3,3,3-hexafluoroisopropyl ether in accordance with claim 5, wherein said solvent has a formula $HO-(CH_2-CH_2-O)_nH$, and where n=1–20.

7. A method for synthesizing fluoromethyl-1,1,1,3,3,3-hexafluoroisopropyl ether in accordance with claim 6, wherein n=8–10.

8. A method for synthesizing fluoromethyl-1,1,1,3,3,3-hexafluoroisopropyl ether in accordance with claim 7, wherein said solvent is a polyethylene glycol having an average molecular weight of 400.

9. A method for synthesizing fluoromethyl-1,1,1,3,3,3-hexafluoroisopropyl ether in accordance with claim 5, where said solvent is selected from the group consisting of N-methyl pyrrolidone, water, t-butanol, higher (i.e., $C \geq 5$) alkyl non-nucleophilic alcohols, and phenols.

10. A method for synthesizing fluoromethyl-1,1,1,3,3,3-hexafluoroisopropyl ether in accordance with claim 5, wherein said solvent is selected from the group consisting of dimethyl sulfoxide (DMSO), dimethyl formamide (DMF), hexamethyl phosphoramide (HMPA), and ethers of polyethylene glycols.

11. A method for synthesizing fluoromethyl-1,1,1,3,3,3-hexafluoroisopropyl ether in accordance with claim 5, wherein combining said intermediate and said second compound is performed in the presence of a co-solvent.

12. A method for synthesizing fluoromethyl-1,1,1,3,3,3-hexafluoroisopropyl ether in accordance with claim 11, wherein said co-solvent is water.

13. A method for synthesizing fluoromethyl-1,1,1,3,3,3-hexafluoroisopropyl ether in accordance with claim 12, wherein said co-solvent is present in an amount of 0.1%–5% w/w relative to said solvent.

14. A method for synthesizing fluoromethyl-1,1,1,3,3,3-hexafluoroisopropyl ether in accordance with claim 1, wherein said first compound is 1,3,5-trioxane, wherein said chlorinating agent is aluminum trichloride, and wherein one molar equivalent of hexafluoroisopropanol is combined with 0.33 molar equivalent of said 1,3,5-trioxane and 1 molar equivalent of said chlorinating agent.

15. A method for synthesizing fluoromethyl-1,1,1,3,3,3-hexafluoroisopropyl ether in accordance with claim 1, wherein 1–5 molar equivalent of said second compound is combined with 1 molar equivalent of said intermediate.

16. A method for synthesizing fluoromethyl-1,1,1,3,3,3-hexafluoroisopropyl ether in accordance with claim 1, wherein said method further comprises dissolving an aluminum hydroxydichloride polymer using an aqueous acid, and wherein said aluminum hydroxydichloride is produced by combining hexafluoroisopropanol and said first compound in the presence of said chlorinating agent.

17. A method for synthesizing fluoromethyl-1,1,1,3,3,3-hexafluoroisopropyl ether in accordance with claim 16, wherein said aqueous acid is aqueous HCl.

18. A method for synthesizing fluoromethyl-1,1,1,3,3,3-hexafluoroisopropyl ether in accordance with claim 1, wherein said method further comprises inactivating an aluminum hydroxydichloride polymer with an alkali metal fluoride, and wherein said aluminum hydroxydichloride is produced by combining hexafluoroisopropanol and said first compound in the presence of said chlorinating agent.

19. A method for synthesizing fluoromethyl-1,1,1,3,3,3-hexafluoroisopropyl ether in accordance with claim 18, wherein said alkali metal fluoride is potassium fluoride.

20. A method for synthesizing fluoromethyl-1,1,1,3,3,3-hexafluoroisopropyl ether in accordance with claim 1, wherein said method further comprises separating an aluminum hydroxydichloride polymer from said intermediate, and wherein said aluminum hydroxydichloride is produced by combining hexafluoroisopropanol and said first compound in the presence of said chlorinating agent.

21. A method for synthesizing fluoromethyl-1,1,1,3,3,3-hexafluoroisopropyl ether in accordance with claim 1, wherein combining hexafluoroisopropanol and a first compound in the presence of aluminum trichloride to produce an intermediate and combining said intermediate and a second compound are performed in a single reaction vessel.

22. A method for synthesizing fluoromethyl-1,1,1,3,3,3-hexafluoroisopropyl ether in accordance with claim 1, wherein combining hexafluoroisopropanol and a first compound in the presence of aluminum trichloride is conducted at a temperature in a range of 0°–22°.

23. A method for synthesizing fluoromethyl-1,1,1,3,3,3-hexafluoroisopropyl ether in accordance with claim 1, wherein said method further comprises distilling said fluoromethyl-1,1,1,3,3,3-hexafluoroisopropyl ether.

24. A method for synthesizing sevochlorane, said method comprising:
    combining hexafluoroisopropanol and a first compound in the presence of a chlorinating agent to produce chloromethyl-1,1,1,3,3,3-hexafluoroisopropyl ether, said first compound being selected from a group consisting of paraformaldehyde and 1,3,5-trioxane, and said chlorinating agent being selected from a group consisting of aluminum trichloride and phosphorous trichloride.

25. A method for synthesizing sevochlorane in accordance with claim 24, wherein said chlorinating agent is aluminum trichloride.

26. A method for synthesizing sevochlorane in accordance with claim 24, wherein said first compound is 1,3,5-trioxane.

27. A method for synthesizing fluoromethyl-1,1,1,3,3,3-hexafluoroisopropyl ether, said method comprising:
    combining hexafluoroisopropanol and 1,3,5-trioxane in the presence of aluminum trichloride to produce an intermediate;
    combining said intermediate and potassium fluoride to produce fluoromethyl-1,1,1,3,3,3-hexafluoroisopropyl ether.

28. A method for synthesizing fluoromethyl-1,1,1,3,3,3-hexafluoroisopropyl ether in accordance with claim 27, wherein combining said intermediate and potassium fluoride is conducted in the presence of a solvent, and wherein said solvent has a formula $HO—(CH_2—CH_2—O)_nH$, and where $n=1–20$.

29. A method for synthesizing fluoromethyl-1,1,1,3,3,3-hexafluoroisopropyl ether in accordance with claim 28, wherein $n=8–10$.

30. A method for synthesizing fluoromethyl-1,1,1,3,3,3-hexafluoroisopropyl ether in accordance with claim 28, wherein said solvent is a polyethylene glycol having an average molecular weight of 400.

31. A method for synthesizing fluoromethyl-1,1,1,3,3,3-hexafluoroisopropyl ether in accordance with claim 28, wherein combining said intermediate and potassium fluoride is conducted in the presence of a co-solvent, said co-solvent comprising water.

32. A method for synthesizing fluoromethyl-1,1,1,3,3,3-hexafluoroisopropyl ether in accordance with claim 31, wherein said co-solvent is present in an amount of 0.1%–5% w/w relative to said solvent.

* * * * *